United States Patent
Alexandre et al.

(10) Patent No.: US 7,261,702 B1
(45) Date of Patent: Aug. 28, 2007

(54) NEEDLELESS SYRINGE OPERATING WITH AN IMPACT WAVE GENERATOR THROUGH A WALL

(75) Inventors: Patrick Alexandre, Gray (FR); Pierre Brunet, Lardy (FR); Brigitte Cagnon, Ballancourt (FR); Claude Mikler, Dijon (FR)

(73) Assignee: Crossject, Paris (FR)

( * ) Notice: Subject to any disclaimer, the term of this patent is extended or adjusted under 35 U.S.C. 154(b) by 374 days.

(21) Appl. No.: 10/018,469

(22) PCT Filed: Jun. 30, 2000

(86) PCT No.: PCT/FR00/01848

§ 371 (c)(1),
(2), (4) Date: Feb. 4, 2002

(87) PCT Pub. No.: WO01/05451

PCT Pub. Date: Jan. 25, 2001

(30) Foreign Application Priority Data

Jul. 16, 1999 (FR) .................................. 99 09255

(51) Int. Cl.
*A61M 5/30* (2006.01)
(52) U.S. Cl. .................... 604/68; 604/69; 604/140
(58) Field of Classification Search ............ 604/60, 604/68, 69, 70, 72, 130, 131, 140, 141, 143, 604/146

See application file for complete search history.

(56) References Cited

U.S. PATENT DOCUMENTS

| | | | | |
|---|---|---|---|---|
| 2,737,946 A | * | 3/1956 | Hein, Jr. ..................... | 604/70 |
| 3,788,315 A | | 1/1974 | Laurens | |
| 3,802,430 A | * | 4/1974 | Schwebel et al. ............. | 604/69 |
| 4,089,334 A | * | 5/1978 | Schwebel et al. ............. | 604/69 |
| 4,124,024 A | * | 11/1978 | Schwebel et al. ............. | 604/69 |
| 4,945,050 A | * | 7/1990 | Sanford et al. ............. | 435/459 |

FOREIGN PATENT DOCUMENTS

| | | |
|---|---|---|
| WO | WO94/24263 | 10/1994 |
| WO | WO96/20022 | 7/1996 |
| WO | WO 96/25190 | 8/1996 |
| WO | WO96/25190 | * 8/1996 |
| WO | WO99/04838 | 2/1999 |

\* cited by examiner

*Primary Examiner*—Catherine S. Williams
(74) *Attorney, Agent, or Firm*—Oliff & Berridge, PLC

(57) ABSTRACT

The technical field of the invention is that of needleless syringes used for intradermal, subcutaneous or intramuscular injections of active principle for therapeutic purposes. More particularly, the invention concerns a needleless syringe (10) comprising a propelling system, the active principle and an application guide (8), mainly characterised in that the propelling system consists of an impact wave generating device (3) and the active principle is arranged in at least a blind cavity (7) of the downstream surface (6) of a barrier (4) extended by the application guide (8). Thus, the active principle is expelled in the form of streamlined jets, driven at very high speed.

10 Claims, 2 Drawing Sheets

NEEDLELESS SYRINGE OPERATING WITH AN IMPACT WAVE GENERATOR THROUGH A WALL

Figure 1:
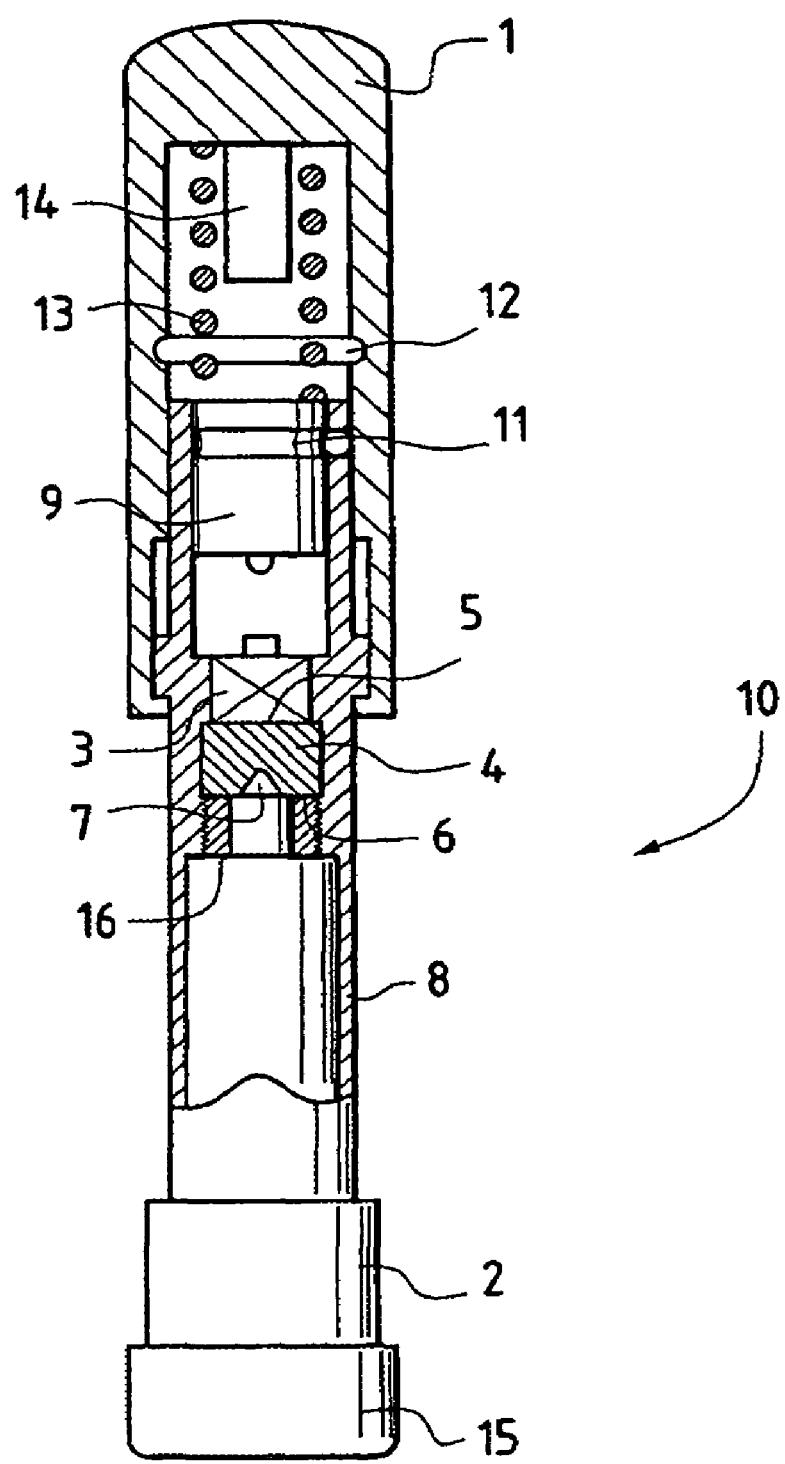

The present invention is in the field of needleless syringes used for intradermal, subcutaneous or intramuscular injections of various active principles for therapeutic use in human or veterinary medicine.

Many types of needleless syringes for injecting liquid active principles have been known since 1945. In these devices, the liquid active principle is delivered, via a nozzle comprising at least one orifice, by a piston or by the deformation of a flexible envelope containing said liquid, said flexible envelope being connected to the nozzle. The injection pressure is obtained either by the release of an initially compressed spring or by the release of a gas stored under pressure, as is describe in U.S. Pat. No. 3,788,315. Other subcutaneous injection devices use a pyrotechnic charge generating gas to propel a piston which delivers the liquid to be injected, and U.S. Pat. No. 3,802,430 illustrates such a technique for generating propellant gas.

For injecting solid active principles in the form of a dry powder, needleless syringes use different means to accelerate the particles of said active principle, and mention must be made of patent application WO 94/242263 which describes a needleless syringe in which the particles of the active principle are entrained by a gas flow at high speed, by means of a compressed gas being released through a tubing. Despite the use of a long tubing, a dispersed cloud of particles is produced, which suggests that there is a low bioavailability. Auxiliary devices also have to be used to dissipate the blast effect and noise of the gas jet. Finally, the reliability of the system depends on that of the device used for storing the gases under pressure.

In another technical field, U.S. Pat. No. 4,945,050 describes the principle of a laboratory apparatus for bombarding a cell culture with metal microparticles coated with various biological substances for purposes of gene transfection. Different means are used in particular to transfer the kinetic energy of a projectile impacting a barrier to the particles arranged on the projectile or on this barrier and to cause these particles to penetrate into the cell culture. This laboratory apparatus operates under a vacuum and uses very dense neutral microparticles to increase the kinetic energy (microparticles of gold or of tungsten), which excludes any application or any transposition as a needleless syringe, especially since it produces a cloud of particles in order to reach the largest possible number of cells.

One of the objects of the invention is to overcome the disadvantages affecting needleless syringes permitting injection of powdered active principle. Another object of the present invention is to make available a more universal syringe which can be used for injection not only of powdered active principles but also of active principles which are liquid, or in suspension in a liquid, or in the form of gel. The transformation of the initial volume of the active principle and its streamlining at the moment of penetration into the skin are obtained by an effect of reversal and focusing which has been discovered and which has been observed in the case of liquids, gels and powders.

The present invention relates to a needleless syringe for injecting active principle for therapeutic use, comprising, from upstream to downstream, a propelling system, the active principle, and an application guide for applying said syringe to the skin of the subject to be treated, this syringe being such that, on the one hand, the propelling system consists of a shock wave generator device and, on the other hand, the active principle is arranged in at least one blind cavity of the downstream face of a barrier continued by the application guide. The barrier has two opposite faces, namely an upstream one, situated toward the shock wave generator device, and a downstream one, situated toward the application guide.

The upstream face of the barrier is substantially plane and transverse. The downstream face of the fixed barrier comprises at least one blind cavity, this cavity thus having an opening only on the downstream face of the fixed barrier and not opening out on the upstream face, thereby providing a thickness sufficient to resist the shock wave.

The shock wave generator device advantageously produces a plane shock wave on the upstream face of the fixed barrier. The plane shock wave produced on the upstream face of the fixed barrier propagates through this barrier and violently ejects the active principle from each of the cavities where it was arranged. Unexpectedly, the active principle thus accelerated at very high speed is able to regroup in the form of a central jet of small diameter which will then penetrate into the skin of the subject. Each jet corresponds to a cavity and has a streamlined shape at its downstream end once the distance traveled by this jet corresponds to several diameters from the fixed barrier. It should be noted that the phenomenon of ejection in the form of jets is fully effective when the shock wave is plane at the moment when it reaches the cavities. This does not exclude the possibility that the shock wave produced on the upstream face may not be strictly plane and may have a slight curvature, which will be eliminated upon propagation in the barrier.

This phenomenon of shaping into a streamlined jet of active principle starting from the principle initially stored in globular form, in all or part of a cavity subjected to a shock wave, can be likened to the jets of substance which result from the detonation of explosive charges having a concave downstream face covered by a metal foil. Such explosive charges, referred to as "hollow charges", make it possible to obtain streamlined shards at high temperature which are propelled at speeds of the order of 8000 meters per second and are capable of piercing armored plating of up to 1 meter in thickness. However, the phenomenon employed in the present invention is of an entirely different nature since the active principle must not in practice experience any increase in temperature and propulsion speeds of the order of 600 to 1000 meters per second are entirely sufficient to permit an injection through the epidermis. In contrast to the explosive charges forming a central jet of substance, the explosive must not be in contact with the substance to be ejected and must be separated by a resistant barrier which ensures a good propagation of the shock wave, which barrier can be made, for example, of aluminum or steel. On account of the limited speed of ejection of the jet of active principle, it was discovered that not only could the shock wave be obtained with a small quantity of explosive whose detonation is triggered by a microdetonator, but that this shock wave could be obtained by other means such as the propulsion of a weight which strikes the upstream face of the fixed barrier.

Advantageously, to obtain a streamlined jet, each blind cavity of the fixed barrier has an opening transverse section which is at least equal to each transverse section of this cavity and preferably each cavity has a form of revolution about an axis parallel to the direction of propagation of the shock wave, with the aim of promoting the formation of a jet which is perfectly aligned on the axis of said cavity.

A cavity can preferably have, for example, a hemispherical, conical or frustoconical shape or can consist of a combination of these profiles.

According to an alternative embodiment, a plurality of cavities are distributed on the downstream face of the barrier. These cavities, which can have different shapes, are advantageously distributed uniformly on said surface.

The active principle is advantageously deposited at the bottom of the cavity and preferably fills the whole cavity until it is flush with the plane part of the downstream face in which it is retained, for example, by means of a thin film. This is because digital simulations have shown that with such a configuration of filling, the diametrical dispersion of the jet is minimal.

The material used for the fixed barrier is chosen from the group of materials which do not give rise to the phenomenon of flaking under the action of a shock wave, such as, for example, metals. It is also chosen on the basis of its density and its acoustic impedance, in other words its ability to transmit the shock wave. It is in particular chosen as a function of the speed one wishes to communicate to the jet.

In a first embodiment, the shock wave on the upstream face of the fixed barrier is produced by the impact, on said upstream face, of a weight of suitable shape which is accelerated by an auxiliary device. The diameter of said weight is advantageously such that the air located between the weight and the fixed barrier is expelled without braking said weight, which is guided by suitable means. The acceleration of the weight is effected either by the release of a compressed spring or by the combustion of a pyrotechnic charge, or by the release of compressed gas.

In a second embodiment, the plane shock wave on the upstream face of the fixed barrier is produced by a shock wave generator which comprises a detonating pyrotechnic charge. The latter advantageously comprises a foil of explosive adjacent to the upstream face, said foil of explosive being triggered either at a point or over all or part of its surface by a microdetonator. This foil of explosive has a diameter substantially equal to that of the fixed barrier and comprises several tens of milligrams of an explosive such as TNT or a composite explosive with a high speed of detonation.

The application guide has a length which is such that it allows the active principle, during its ejection toward the skin, to regroup in the form of a streamlined jet. The length of the application guide is advantageously between 1 and 8 times the diameter of the fixed barrier and preferably between 2 and 5 times the diameter of the fixed barrier.

The application guide advantageously comprises a shock absorbing system which can be reduced to a simple flexible flange situated at its end bearing on the skin of the subject to be treated, or can consist of a telescopic application guide with an inner spring.

The present invention satisfactorily solves the problems posed and makes it possible, for example, to obtain, for a barrier of 5 mm diameter and 2 mm thickness, jets of diameters between 0.12 mm and 1.6 mm when use is made of ogival, substantially hemispherical or conical cavities, although in the case of conical cavities in particular it is advantageous if the downstream face of the active principle is plane and does not exceed 3 to 4 mm in diameter.

For a barrier with a diameter of 5 millimeters, a thickness of 3 millimeters and a hemispherical cavity of one millimeter radius, using an explosive pellet with a diameter of 3 millimeters and a thickness of 1 millimeter, it is possible to obtain a jet having a maximum diameter of 0.7 millimeter with a speed of ejection of 630 meters per second.

The major effect sought using the ejection device according to the invention is an attenuated effect referred to as "hollow charge" which translates into the formation of a streamlined jet composed of the particles of substance to be expelled, and driven, on its axis, at a very high speed which gives it a high force of penetration. The characteristics of this jet, namely its shape, its length, its dispersion and its speed of displacement are a function of the nature and positioning of the generator of plane waves, the material constituting the part serving as barrier, and the geometry of the cavities in the downstream face serving to accommodate the particles. At a lower level, the general shape of the volume formed by the particles in each cavity also plays a role.

Advantageously, under the effect of the pyrotechnic charge, the barrier, although having been deformed, remains fixed in the syringe at its original position. According to another embodiment of the invention, when confronted by the same stress the barrier is displaced but remains trapped in the syringe without any possibility of being expelled.

The application guide is preferably made up of a hollow cylindrical body whose cross section is similar to that formed by the downstream face of the barrier and whose axis is perpendicular to said face. This guide is particularly recommended for optimizing the conditions for achieving a perpendicular impact on said surface.

According to a first embodiment of the invention, the particles form a mass of powder in each cavity. These particles are held in their seat by capillarity, by static electricity, by an adhesive surface state or by a membrane covering each cavity. Finally, any means of adhesion can be used, provided that it does not interfere with the formation of the jet.

According to a second embodiment of the invention, the particles are bound to each other by a liquid which is fluid, viscous or in the form of a gel. In relation to this liquid, the particles of active principle can be either in suspension or in solution.

Advantageously, the trigger can be a push button which initiates the microdetonator by percussion.

The device according to the invention has the advantage of being efficient while having a simple and lightweight design which takes up little space. This is because the technique involving the formation of a jet using the hollow charge model allows particles to be projected in concentrated form and at very high speed from a device having a small number of components made of lightweight materials and arranged in a simple manner in relation to one another.

Moreover, a rapid dimensioning makes it possible to adapt the device to a wide range of situations, by acting in particular on the cross section of the jet, its dispersion, its length, its speed, and the number of jets to be expelled.

Furthermore, as the active principle is not set in motion by the release of the gases, there is no hissing effect. Nor is there any noise associated with the release of the gases to the outside, the noise only possibly originating from the impact of the weight on the barrier or from the functioning of the pyrotechnic charge, which are internal to the syringe.

The present invention will now be described in more detail with the aid of FIG. 1 which shows a partial cross-sectional view of a syringe according to the invention and which can be used to describe two shock wave generators.

FIG. 1 shows a view of a syringe 10 before use, the downstream end of this syringe 10 still being closed by a hermetic stopper 15 which ensures asepsis of the inner part of the application guide 8.

According to this FIG. 1, the application guide 8 is continued inside the trigger tube 1 and comprises, from downstream to upstream, a threaded ring 16 which ensures the immobilization of a fixed barrier 4 located entirely within the application guide 8 on a shoulder of the guide, this shoulder forming a central opening in which the shock wave generator device 3 is placed, formed by a pellet of sensitive composite explosive, surmounted by a microdetonator which can be initiated by percussion. A weight 9 is able to slide in the internal continuation of the application guide 8 and comprises a striker pin at its downstream end and a retainer groove 19 in which there are engaged three balls 11 (two shown) placed in radial perforations 18 of this continuation. These balls 11 bear on the inner surface of the trigger tube 1 and immobilize the hollow weight percussion 9 surmounted by a spring 13 compressed between this weight 9 and the bottom of the trigger tube 1, this tube 1 being held in the initial position by a lower internal shoulder in contact with the application guide 8.

The powdered active principle fills a semi-ellipsoid cavity 7 situated on the downstream face 6 of the barrier 4, and this principle is held by means of a thin film secured on the fixed barrier 4 and wedged by the threaded ring 16.

In operation, after the stopper 15 has been removed and the freed end of the application guide 8 has been applied in contact with the area of the epidermis chosen for injection of the active principle, the trigger tube 1 is pressed in order to compress the spring 13 until the inner groove 12 of this tube 1 arrives at the level of the three balls 11 which spread apart radially and release the hollow percussion weight 9 whose downstream point will strike the microdetonator, causing the explosive pellet in contact with the upstream face 5 of the fixed barrier 4 to explode. The plane shock wave thus generated will reach the cavity 7 and simultaneously provoke the rupture of the thin film and the ejection of the active principle on the basis of a phenomenon of reversal and focusing similar to the phenomenon employed in hollow charges. The hollow weight 9, the spring 13 and the material 14 then have the function of absorbing the effects behind the detonation, and the shock absorbing system 2 of the application guide 8 attenuates the effect of compression in front, this sensation of annular compression largely masking the pricking sensation resulting from the penetration of the streamlined jet of active product into the epidermis and dermis.

Figure 2:
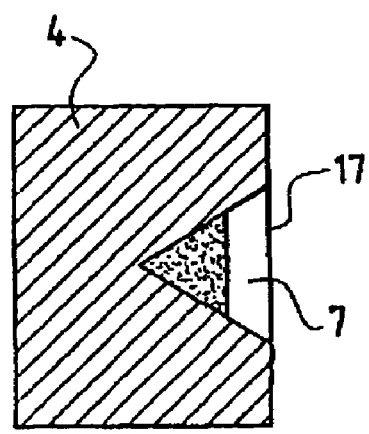

FIG. 2 is an enlarged longitudinal cross-section of the barrier 4, showing an opening transverse section 17 that is greater than each transverse section of the cavity 7.

Figure 3:
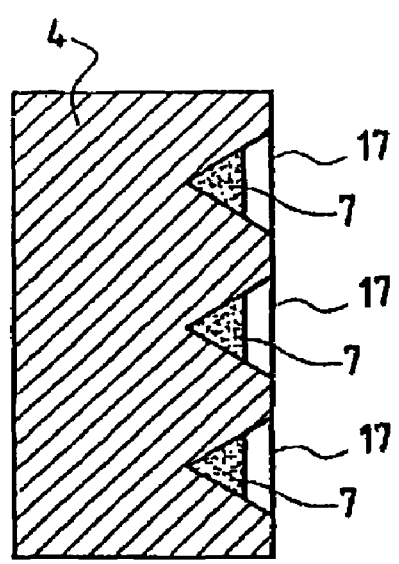

FIG. 3 shows another enlarged longitudinal cross section of the barrier 4, showing a plurality of cavities 7, each with an opening transverse section 17.

According to an alternative embodiment which can be described with reference to this same figure, the plane shock wave is not produced by an explosive in contact with the barrier 4 in which the blind cavity 7 is formed. This alternative (not shown) requires the use of a solid weight which is continued downstream by a cylindrical striking peen which can engage in the bore obtained by removing the explosive and the detonator so as to strike the fixed barrier 4 directly. In this alternative, the spring 13 is not useful and the material 14 must be replaced by a pyrotechnic gas generator which can be activated by an external means, the trigger tube 1 being completely integral with the application guide 8 and comprising an internal sheath deformable at the level of the three balls 11. In operation, the initiation of the pyrotechnic gas generator ensures a pressure increase in the chamber between the trigger tube and the weight, until the pressure exerted on this weight causes the partial engagement of the three balls in the deformable sheath and frees this weight, of which the peen will strike the fixed barrier 4 and will generate a plane shock wave with which it is possible to obtain the formation of a streamlined jet of the active product initially stored in globular form in the blind cavity 7.

The invention claimed is:

1. A needleless syringe for injecting an active principle, comprising:
    a propelling system including a shock wave generator device;
    an application guide for applying said syringe to the skin of the subject to be treated; and
    a resistant barrier which ensures an effective propagation of a shock wave through the resistant barrier, and is located entirely within the application guide, and comprises an upstream face and a downstream face, said downstream face having at least one blind cavity in which the active principle is accommodated, the resistant barrier remaining fixed within the syringe during injection, wherein the resistant barrier has a first position before injection and the first position is substantially maintained after injection; and
    wherein the shock wave generator device is configured to deliver a shock wave to the upstream face of the barrier.

2. The needleless syringe as claimed in claim 1, wherein the upstream face of the resistant barrier is substantially plane and transverse.

3. The needleless syringe as claimed in claim 1, wherein the shock wave generator device produces a plane shock wave on the upstream face of the resistant barrier.

4. The needleless syringe as claimed in claim 1, wherein the at least one blind cavity has an opening transverse section which is greater than each transverse section of the at least one blind cavity.

5. The needleless syringe as claimed in claim 1, wherein the at least one blind cavity has a form of revolution about an axis parallel to the direction of propagation of the shock wave.

6. The needleless syringe as claimed in claim 1, wherein the at least one blind cavity comprises a plurality of cavities distributed on the downstream face of the resistant barrier.

7. The needleless syringe as claimed in claim 1, wherein the shock wave generating device comprises a detonating pyrotechnic charge.

8. The needleless syringe as claimed in claim 1, wherein the length of the application guide is between 2 and 5 times the diameter of the resistant barrier.

9. The needleless syringe as claimed in claim 8, wherein the application guide comprises a shock absorbing system.

10. The needleless syringe as claimed in claim 1, wherein the length of the application guide is between 1 and 8 times the diameter of the resistant barrier.

* * * * *